US006706977B2

(12) United States Patent
Cain et al.

(10) Patent No.: US 6,706,977 B2
(45) Date of Patent: Mar. 16, 2004

(54) SELF-MONITORING CONTROLLER FOR QUARTZ CRYSTAL MICROBALANCE SENSORS

(75) Inventors: Russell P. Cain, Columbia, MD (US); Bliss G. Carkhuff, Laurel, MD (US); O. Manuel Uy, Ellicott City, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 10/227,928

(22) Filed: Aug. 26, 2002

(65) Prior Publication Data

US 2002/0189868 A1 Dec. 19, 2002

Related U.S. Application Data

(62) Division of application No. 09/703,461, filed on Nov. 1, 2000, now Pat. No. 6,492,601.
(60) Provisional application No. 60/162,792, filed on Nov. 1, 1999.

(51) Int. Cl.[7] .............................. G01G 3/14; G01N 29/02
(52) U.S. Cl. .............................. 177/210 FP; 177/210 R; 73/580; 73/24.01; 310/315; 310/342
(58) Field of Search ....................... 177/210 R, 210 FP, 177/DIG. 11; 73/24.01, 24.05, 24.06, 28.01, 579, 580, DIG. 1, DIG. 4; 310/315, 341, 342, 343; 62/3.2; 324/537, 760

(56) References Cited

U.S. PATENT DOCUMENTS

| | | | | |
|---|---|---|---|---|
| 3,926,271 A | * | 12/1975 | Patashnick | 177/210 FP |
| 4,561,286 A | * | 12/1985 | Sekler et al. | 73/24.06 |
| 4,858,145 A | * | 8/1989 | Inoue et al. | 177/210 FP |
| 5,232,063 A | * | 8/1993 | Stoller | 177/210 FP |
| 5,369,979 A | * | 12/1994 | Aylsworth et al. | 73/24.01 |
| 5,473,259 A | * | 12/1995 | Takeda et al. | 324/760 |
| 5,604,335 A | * | 2/1997 | Isahaya | 177/210 FP |
| 5,684,276 A | * | 11/1997 | Altemir | 177/210 FP |
| 5,706,840 A | * | 1/1998 | Schneider et al. | 134/56 R |
| 5,869,763 A | * | 2/1999 | Vig et al. | 73/580 |
| 5,982,189 A | * | 11/1999 | Motika et al. | 324/763 |
| 6,184,504 B1 | * | 2/2001 | Cardella | 219/513 |
| 6,262,584 B1 | * | 7/2001 | Kurosu et al. | 324/760 |
| 6,444,927 B1 | * | 9/2002 | Korpi | 177/210 FP |

OTHER PUBLICATIONS

"Superfluid Helium Film in Zero Gravity", L. C. Yang & P. V. Mason, XP–002157668, JPL Cal. Tech., Jul. 7, 1979.*
"A Microprocessor–Based Piezoelectric Quartz Microbalance System for Compound–Specific Detection", P. Killnkhachorn et al., IEEE Transactions on Instruments & Measurement 39, No.1, NY, US, Feb. 1990.*
"NASA Technical Briefs", Mechanical Engineering, vol. 90, p. 44, Jan. 1976.*
"High–precision low–cost quartz–crystal thin–film monitor with temperature control", G. Kremer, Rev. of Scientific Instruments 56, No. 7, Woodbury NY, pp. 1467–1468, Jul. 1985.*

* cited by examiner

Primary Examiner—Randy Gibson
(74) Attorney, Agent, or Firm—Albert J. Fasulo, II (57) ABSTRACT

A controller for a quartz crystal microbalance (QCM) sensor system and method for detecting mass deposition on a QCM sensor. The controller controls a QCM using temperature-, voltage- and current-regulating circuits, a microcontroller, an oscillator, heating and cooling devices and circuits, high voltage grids, digital-to-analog and analog-to-digital converters, data telemetry and uplink circuits, and a remote user. The remote user may be a person, computer, network or data logger. The remote user allows the controller to be reconfigurable during operation. The controller samples and reports data faster and is more reliable over extended periods of operation. Further, the controller is assembled using innovative techniques making it smaller and thus more transportable, easier to incorporate into existing facilities and less expensive to construct and operate. The apparatus may also be assembled in a modular fashion that allows for customization.

2 Claims, 7 Drawing Sheets

SELF-MONITORING CONTROLLER FOR QUARTZ CRYSTAL MICROBALANCE SENSORS

CROSS REFERENCE TO RELATED APPLICATION

This application is a divisional of the U.S. application Ser. No. 09/703,461, filed Nov. 1, 2000, now U.S. Pat. No. 6,492,601B1 and claims priority from U.S. Provisional Application No. 60/162,792, filed Nov. 1, 1999, both of which applications are hereby incorporated by reference.

BACKGROUND OF THE INVENTION

1. Field of the Invention

The present invention relates to the field of electronic control circuits for microelectronic measuring devices. Specifically, the invention relates to software-driven microcontroller and electronic circuits for monitoring and controlling quartz crystal microbalance (QCM) sensors, which are highly accurate devices for detecting minute quantities of mass deposited on the face of a crystal.

2. Description of the Related Art

QCM systems have been used for over two decades to measure minute quantities of mass. The principal components of a QCM system include a QCM sensor, an oscillator and control circuitry. In a QCM sensor there are typically two carefully matched quartz crystals aligned parallel to each other and separated by a small gap. Only one of the crystals, however, is exposed to the outside environment. The difference in frequency between the two crystals is the beat frequency, which is a very sensitive indication of the mass being deposited on the exposed crystal surface. The beat frequency is proportional to the mass of contamination that has accumulated on the sensing area and is electronically recorded in a digital electronic counter. Because QCM systems can measure very small amounts of mass deposited, they are often used when precise control over a system or process is desired or to monitor an environment.

QCM sensors have been used in spacecraft, for example, to measure film deposition on sensitive surfaces such as optical mirrors, thermal radiators and solar arrays. They have also been used in gas detection systems to measure contaminant concentrations in an ambient or closed environment. Still other QCM sensors have been used in semiconductor processing to precisely control chemical deposition in vacuum chambers and to monitor clean room contamination.

Control circuits associated with QCM sensors have been used almost as long as QCMs have existed. Conventional controls include an assembly of circuitry and sensors which may or may not consist of a QCM sensor signal conditioner, a QCM sensor temperature monitor, a thermal-electric heat pump controller and a microcontroller for data acquisition and data formatting. These elements have been collectively referred to as QCM controllers, controllers, or control circuits.

Requirements for control circuits are as varied as the applications for the QCM sensor. For example, QCM sensors that are moved in and out of a liquid environment have been fitted with controllers adapted to measure the sensor's resonant frequency over a wide range of impedance. Other QCM sensors that are used to measure the mass of a substantial drop of liquid or particulate matter have been designed to correct for significant viscous damping losses. Still other QCM sensors that are used to monitor chemical environments have been constructed with control circuits that trigger an alarm and warning system. These controllers are typically constructed in large housing units with control panels and readout devices that impose significant weight and power resource requirements. As in most applications, the QCM sensor and controller are accessible; therefore, self-monitoring and wireless telemetry are not needed. Further, present controllers merely control the QCM sensor temperature. Additionally, conventional systems generally require a user to upload commands off-line or directly into the controller from a key-pad on the face of the controller box or from a key-board connected to a computer that is connected to the controller.

As QCM systems have found their way into spacecraft, missiles, and chemical applications, the need for small, lightweight, reliable, cost-effective, remotely-accessible systems capable of operation in extreme low temperatures has been observed. Further, in addition to determining mass, it is highly desirable to determine the electronic charge of particles and the molecular species of the material deposited on the QCM sensor's quartz crystal. Current QCM systems do not include these desirable features.

SUMMARY OF THE INVENTION

It is an object of the invention to provide for the monitoring and control of a microelectronic sensor system.

It is a further object of the invention to provide an apparatus that self-monitors the health of one or more QCM sensors using a microcontroller with computer program instructions capable of controlling the QCM sensor temperature and monitoring the QCM temperature, beat frequency and controller operations, among other things.

It is another object of the invention to provide for a communications system using data telemetry and uplink circuits that allow a remote user to retrieve processed data and to send commands as needed to ensure proper operation of the QCM sensor system or allow the software-driven microcontroller to make adjustments.

It is still another object of the invention to provide for extended operations without taxing finite weight, energy and cost limits such as those imposed in space flight operations.

It is still another object of the invention to operate at extreme cold temperatures, such as those experienced in outer space.

It is still another object of the invention to capture electronic signals including, but not limited to QCM beat frequency, duty cycle, and amplitude and QCM sensor and controller temperature current, convert the signals to data records and then report the data quickly to a remote user to enhance the system's capability and reliability over conventional systems.

It is still another object of the invention to provide a controller using innovative nano-connectors and miniature wiring to achieve a 100-fold reduction in size compared to conventional controllers thereby making the present invention portable and easy to incorporate into existing facilities that have limited space. This also provides for reduced construction and operating costs.

It is still another object of the invention to be assembled in modular units thereby being highly flexible.

It is a further object of the present invention to provide a controller that is modifiable by a user so that it can be reconfigurable during operation.

These and other objects of the invention are described in the description, claims and accompanying drawings and are accomplished by a controller, for controlling an apparatus including a microelectronic sensor and for conditioning electronic signals having associated therewith electronic circuits and self-monitoring software. The controller includes a controller thermal monitor for detecting a temperature of the apparatus and outputting a controller temperature signal, a first temperature measuring circuit for detecting the controller temperature signal from the controller thermal monitor, a second temperature measuring circuit for detecting a temperature signal from the microelectronic sensor and outputting a current signal, a signal conditioning circuit for receiving and conditioning a beat frequency signal from the microelectronic circuit, a microcontroller, connected to the controller thermal monitor, the first and second temperature measuring circuits, and the signal conditioning circuit, for converting the controller temperature signal, the microelectronic sensor temperature signal, the current signal, an amplitude of the beat frequency signal, a voltage from the microelectronic sensor, and the beat frequency signal into data records and for manipulating the data records for transmission. The controller can also include a thermal-electric heat pump circuit, connected to the microelectronic sensor and the second temperature sensing circuit, for detecting the temperature signal from the second temperature sensing circuit and outputting an electric current and for heating and cooling the microelectronic sensor by switching the direction of the electric current, and a power switch for energizing the microelectronic sensor.

The present invention also includes an apparatus for controlling a microelectronic sensor and conditioning electronic signals having associated therewith electronic circuits and self-monitoring software, including a sensor circuit, for precisely detecting temperature and minute changes in mass deposition and outputting a temperature signal associated with a temperature and outputting a beat frequency signal proportional to said mass deposition and a controller circuit for monitoring the health of the sensor means and conditioning the beat frequency signal. The controller circuit can include a controller thermal monitor for detecting a temperature of the controller circuit and outputting a controller temperature signal, a first temperature measuring circuit for measuring the controller temperature signal from the controller thermal monitor, a second temperature measuring circuit for detecting the temperature signal from the sensor circuit, a thermal-electric heat pump circuit for receiving an electric current and for raising or lowering the temperature of the sensor circuit by switching direction of the electric current to the thermal-electric heat pump and for turning off the heat pump, a signal conditioning circuit for receiving and conditioning the beat frequency signal from the sensor circuit and a microcontroller, connected to the controller thermal monitor, the first and second temperature measuring circuits, the thermal-electric heat pump circuit, and the signal conditioning circuit, for converting the controller temperature signal, the sensor circuit temperature signal, the second temperature measuring circuit current, beat frequency and amplitude, microelectronic sensor voltage, and the beat frequency signal into data records and for manipulating said data records for transmission.

The sensor circuit can be any QCM.

The controller circuit can further include a remote user for providing commands remotely, a power switch for energizing power to the sensor circuit, an uplink circuit for receiving commands from the remote user and a telemetry circuit for capturing data records and transmitting data records to the remote user.

The thermal monitor can be a platinum resistive temperature device, a thermocouple, or other thermal monitor device.

The sensor circuit can further include a high voltage grid for attracting specific charged particles for mass measurement by switching a polarity of the high voltage grid to either positive or negative with reference to ground and an insulator for insulating the sensor circuit from the electric current from the high voltage grid and the sensor circuit.

The apparatus may be part of a system that is used in a chemical deposition process, space flight operations, to monitor for chemical contamination in an enclosed or ambient air environment, and/or for biological detection.

The apparatus may include a computerized method for controlling a QCM sensor, the method includes the steps of initializing system variables and establishing default and set-point values; energizing a potential across QCM sensor system terminals, thereby energizing QCM sensor quartz crystals, a thermal-electric heat pump, and a high voltage grid contained within the QCM sensor; detecting the voltage signal amplitude and voltage signal frequency of the QCM sensor system quartz crystals, the voltage amplitude of the QCM sensor system thermal monitor, and the current of the controller thermal monitor and QCM sensor power supply, and producing individual signals representative thereof; amplifying the quartz crystal voltage amplitude signal and calculating the duty cycle and waveform thereof, supplying the previous signals and the calculated duty cycle and waveform calculated above to a microcontroller for conversion into data records; comparing the data records to the default or set-point values; adding synchronization codes to the data records; transmitting the data records through a wired or wireless communications system to a remote computer or computer network; receiving incoming commands from the remote computer or computer network; and adjusting the voltage supply to the thermal-electric heat pump as a result of the incoming commands of the deviation from the default or set-point values. Moreover, the method may also include the steps of slowly heating the QCM sensor quartz crystals and detecting the voltage signal amplitude and voltage signal frequency of vibration of the QCM sensor system quartz crystals over time; calculating a sublimation and evaporation temperature corresponding to the material deposited on the QCM quartz crystal; and supplying the voltage signal amplitude and voltage signal frequency associated with the QCM sensor system quartz crystals and the sublimation and evaporation temperature corresponding to the material deposited to the microcontroller for conversion into data records.

DETAILED DESCRIPTION OF THE INVENTION

Figure 1:
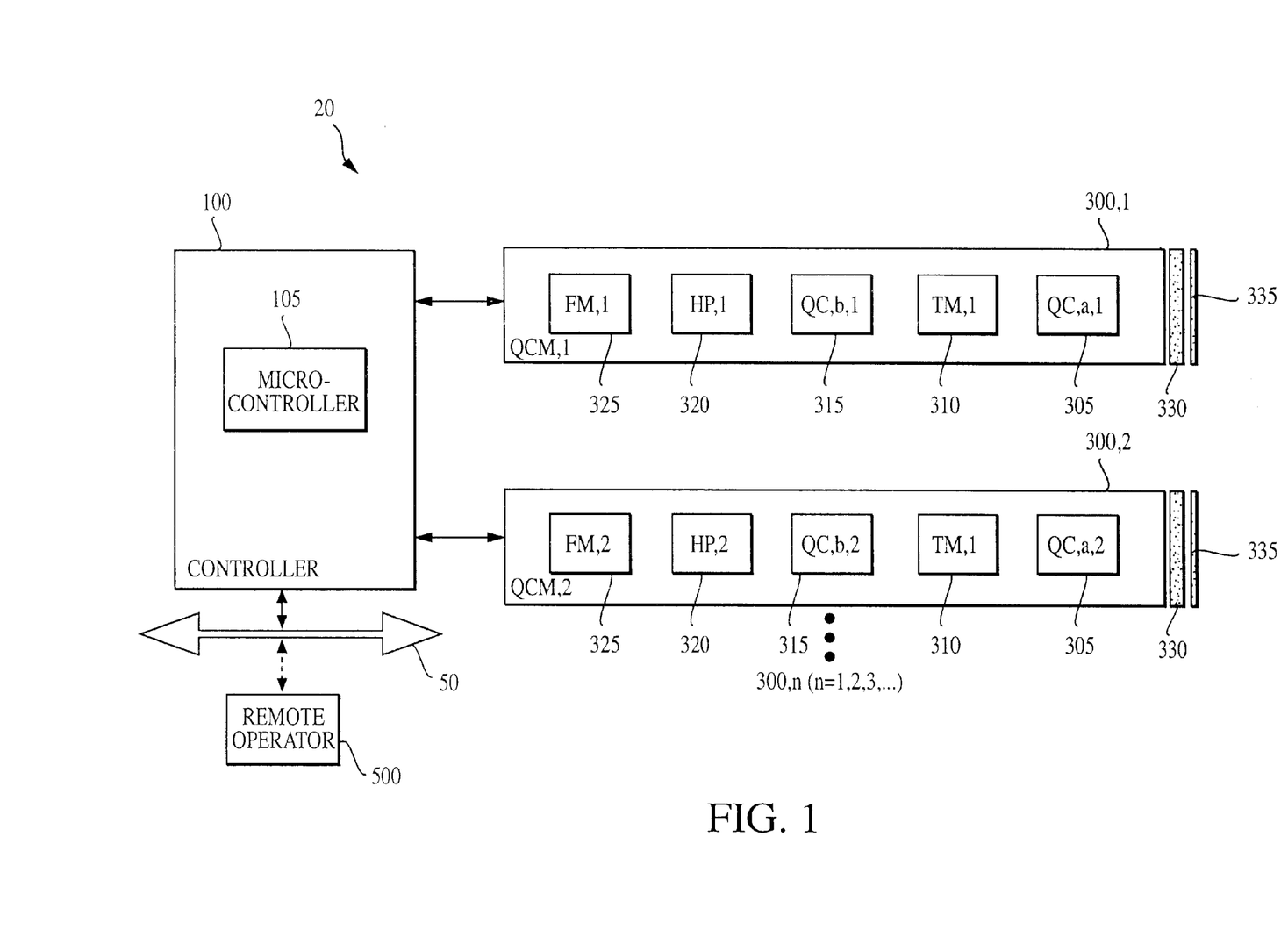
FIG. 1 is a block diagram of an example of a QCM sensor system according to the present invention.

FIG. 1 is a block diagram of a QCM sensor system 20 according to the present invention, which comprises a bus 50, a controller 100, which includes a microcontroller 105, one or more QCM sensors 300, and a remote user 500. In this example, the controller 100 and QCM sensors 300 may be connected by nano-connectors or miniature wiring 340 (FIG. 5) to reduce the size and weight of the QCM sensor system 20.

The QCM sensor system 20 can provide both analog and digital telemetry streams of monitored and processed data. Miniaturized connections 340 (FIG. 5) used between system components are, for example, produced by Nanonics Corp.; however, any equivalent connectors can be used.

Data are transferred through the bus 50 at preferably eight- or sixteen-bit transfer rate and at a frequency consistent with the data sampling and telemetry rate of the system.

The controller 100 can support multiple QCM sensors 300. In many instances, two QCM sensors 300 are practical, and in this example, two sensors 300 are controlled.

Each sensor 300 may include first and second quartz crystals 305 and 315 (QC,a and QC,b), respectively, a thermal (temperature) monitor 310 (TM), thermal-electric beat pump 320 (HP) for adjusting sensor temperature, a frequency mixing circuit 325 (FM), which receives signal from the quartz crystals 305 and 315 and outputs a beat frequency signal, a high voltage grid 335 and an insulator 330. According to the present invention, two quartz crystals are used. The invention, however, can be modified to include a single crystal deposition monitor where there is only one quartz crystal and a thermal electric heat pump is not used. The thermal-electric heat pump 320 is not required in some applications and may be omitted. In some applications, the QCM sensor system 20 may need to operate in extreme low temperatures and should, therefore, be assembled accordingly.

The remote user 500 may include, but not limited to, a computer, computer network data logger and/or a person. The remote user 500 can send software commands to the microcontroller 105.

Figure 2:
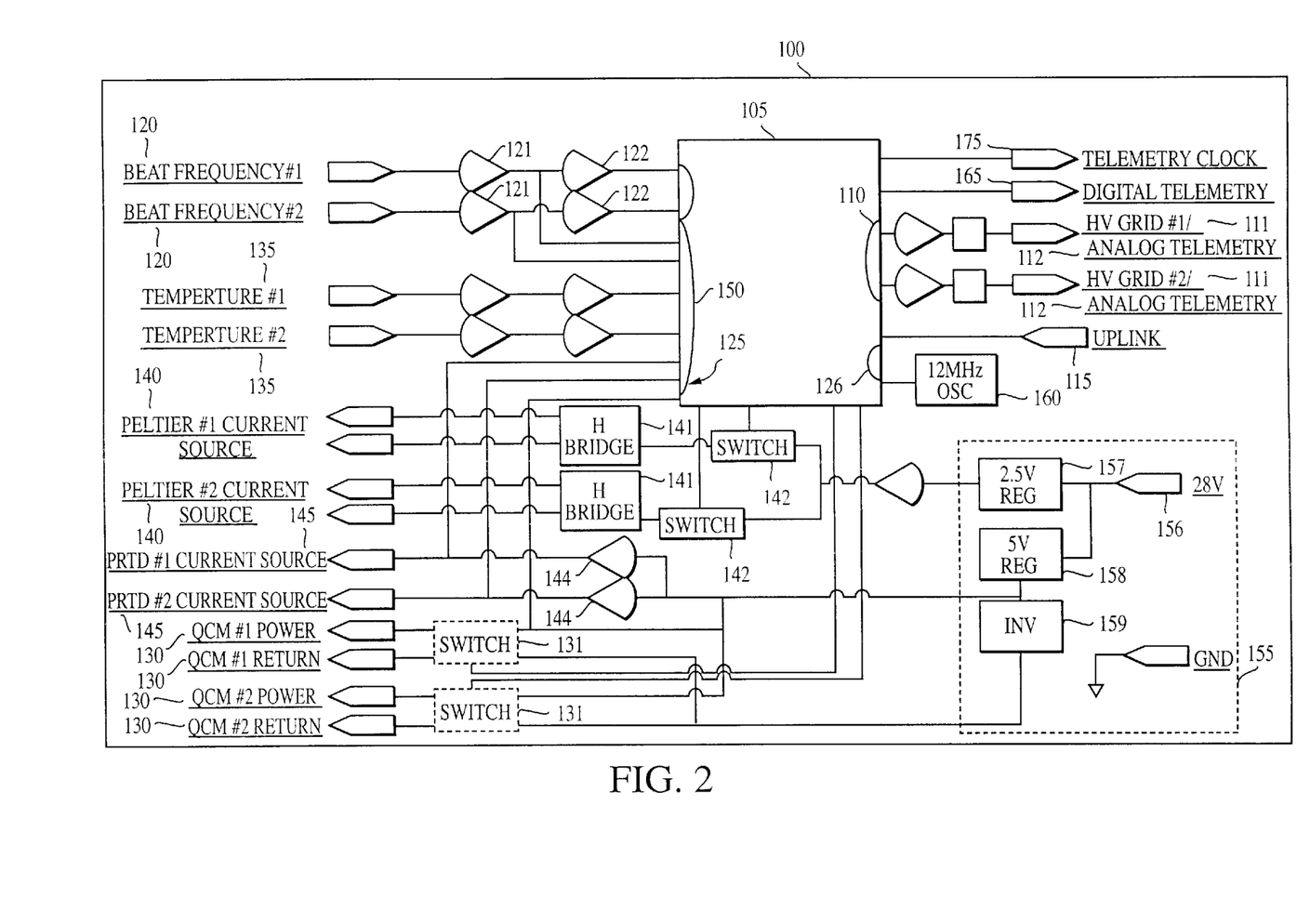
FIG. 2 is a block diagram of an example of a QCM controller apparatus that is part of the QCM sensor system according to the present invention.

FIG. 2 is a block diagram of an example of a QCM controller 100 according to the present invention, shown controlling and monitoring two QCM sensors 300. The controller 100 includes a microcontroller 105, such as an AduC812, 8051 (Intel), or any other chip, which can control, whether internally or externally, any or all of the following: two digital-to-analog converters 110, an analog signal multiplexer 125, thermal hear pump circuits 140 and high voltage grids 111. The microcontroller 105 may also control QCM power switches 131.

The microcontroller 105 monitors frequency amplitude of the beat frequency signal form the QCM sensors 300, two QCM thermal monitoring signal conditioning circuits from thermal monitors 310, one QCM power source 158, the microcontroller temperature monitor 150, two thermal monitoring current sources 144, at least one analog-to-digital converter 126 and, if needed, an analog signal multiplexer 125.

The microcontroller also provides a command interface uplink 115 and data down links 175, 165, or 112, and is responsible for data acquisition and formatting.

The digital-to-analog converters 110 can support a high voltage grid circuit 111, which is coupled to the high voltage grid 335 (FIG. 5), or perform analog telemetry 112. The high voltage grid 335 is provided over the QCM face to getter ionic contamination and can be controlled from approximately plus or minus 200 volts.

The command interface uplink 115 supports uplink command, control, calibration and test functions. The beat frequency signal conditioning circuits 120 include output-limiting amplification circuits with limiters 121 and zero crossing detectors 122, for amplifying small beat frequency signals. Amplification is limited to no greater than plus five volts (+5 volts) in this example because this is the range of the microcontroller inputs. The beat frequency signal conditioning circuit 120 receives the beat frequency signal from frequency mixing circuit 325 (FIG. 1).

The QCM power circuit 130 supplies power to one or more QCM sensors 300. Each QCM power circuit 130 can include QCM power switches 131 for isolating power to one or more of the QCM sensors 300.

The thermal-electric heat pump circuit 140 may be Peltier heat pumps or any type of temperature-regulating device that lowers or raises the QCM temperature to provide better accreation and that also supports thermogravimetric analysis (TGA). In this example, each thermal-electric heat pump circuit 140 includes a thermal-electric heat pump controller 141 and switch 142, which switches current flow through the thermal-electric heat pump circuit 140 (141, 142). Depending on which direction the current flows, the thermal-electric heat pumps 320 (FIG. 1) will either heat or cool the QCM quartz crystals 305 and 315.

The QCM thermal monitor sources 145, including thermal monitoring current sources 144, are coupled to QCM thermal monitors 310, which can be platinum resistive temperature devices (PRTDs), thermocouples, or equivalent devices consistent with the operation of the present invention. The QCM thermal monitors 310 are powered by the QCM thermal monitor sources 145, which include the thermal monitoring current sources 144.

The power system 155 includes, in this example, a 28-volt source 156, 2.5-volt DC-to-DC converter 157, which supplies the thermal-electric heat pump circuit 140, a 5-volt DC-to-DC converter 158, and +5 to −5 volt inverter 159. The converter 157 and 158 and inverter 159 may be substituted, as needed, to accommodate various voltage sources.

In the present example, the oscillator 160 operates at 12 MHz, although it could operate at any frequency that is necessary for the parameters of the circuit. The digital and analog data telemetry signals 112, 165, and 175, can be transmitted using, for example, I2C (Phillips), RS-232 or equivalent serial communications systems protocols. The telemetry stream may contain Hamming codes, or equivalent, for synchronizing data frames, and can be transmitted at 2400 baud or higher. Both signal formats include the system's self-monitoring health data of QCM beat frequency, temperature, voltage amplitude, and duty cycle; current at the QCM thermal monitor 145 from the thermal monitoring current sources 144, the QCM voltage supply 130, and the controller's internal temperature from the microcontroller temperature monitor 150.

Figure 3A:
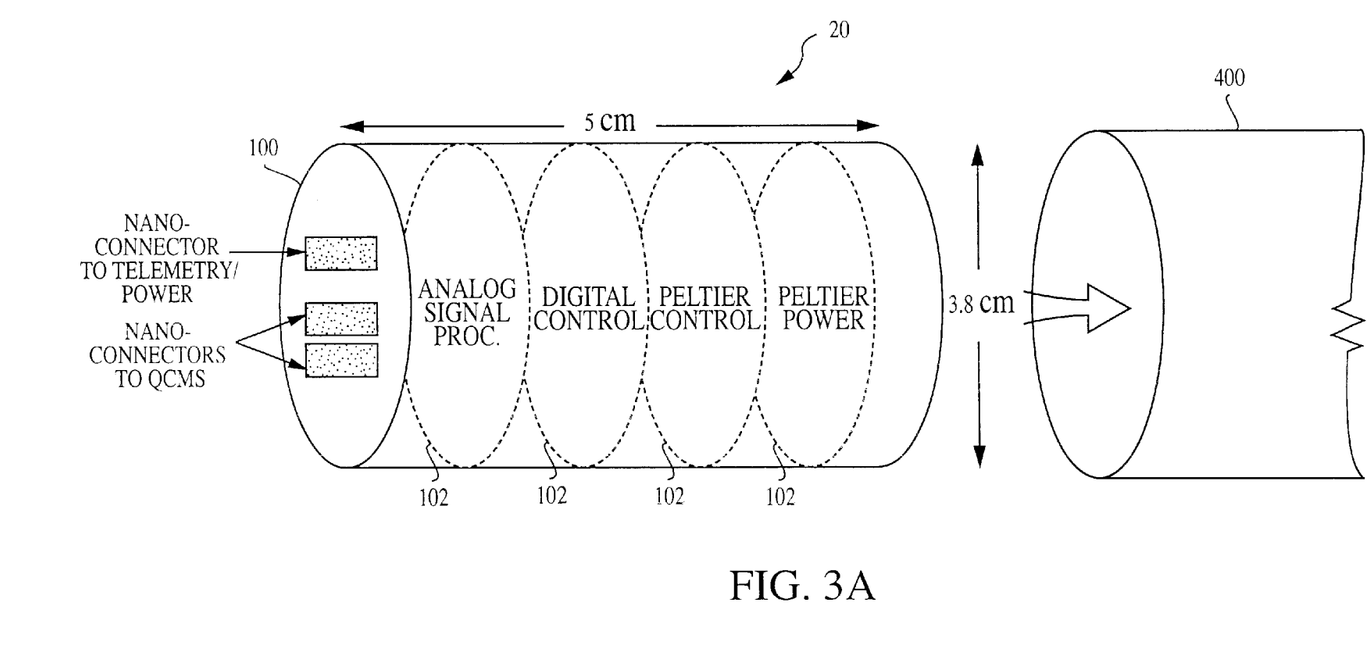
FIG. 3A is a three-dimensional diagram of the physical apparatus of the QCM sensor system according to the present invention.

In this example, the microcontroller 105 has a software-defined sampling rate. It is connected to the QCM power circuit 130, QCM thermal monitor signal conditioning circuits 135, thermal-electric heat pump circuits 140, quartz crystal thermal monitor sources 145, and microcontroller temperature monitor 150. The microcontroller 105 implements program instructions for converting signals into data records and for adding codes to the records for data telemetry synchronization purposes. The microcontroller 105 further implements instructions for recording data for subsequent analysis using standard TGA techniques. In accordance with the disclosed invention, for example, the microcontroller 105 instructs the thermal-electric heat pump circuits 140 to heat or cool the QCM sensor 300 by energizing the thermal-electric heat pumps 320 (FIG. 1) while simultaneously measuring the beat frequency signal from the beat frequency signal conditioning circuits 120 and the signals from the QCM thermal monitor signal conditioning circuit 135. The sublimation and evaporation temperature of a substance can be used to identify the molecular composition of the material based on data recorded in the QCMs. The microcontroller 105 also implements program instructions for measuring the duty cycle associated with the beat frequency signal conditioning circuit 120. The duty cycle provides additional information about the deposition of mass on the QCM sensor 300; it is useful because in some instances the frequency of the beat frequency may not change when liquid is deposited on the first quartz crystal 305. FIG. 3A is a three-dimensional diagram of the physical apparatus of one example configuration of the QCM sensor system 20 showing the electronic controller 100. FIG. 3A shows a modular three-dimensional assembly having controller 100 and associated circuit boards 102 stacked one on top of the other. The circuit boards 102 can be connected with flexible connectors, such as wiring, pin connectors or any other connectors that are consistent with and support the circuit layout on individual boards. By assembling the circuit boards 102 in this manner, the controller 100 may be easily inserted within a housing 400 that provides environmental control. In addition, this assembly allows easy configuration by replacing one or more circuit boards 102, depending on the particular function of the QCM.

The housing 400 may be fabricated from a metal composite that includes, but is not limited to, aluminum, tungsten and titanium. It may also be fabricated from any other appropriate metal or non-metal composite. A radiation shielding material is preferred where the sensor system 20 is used in space flight operations.

Figure 3B:
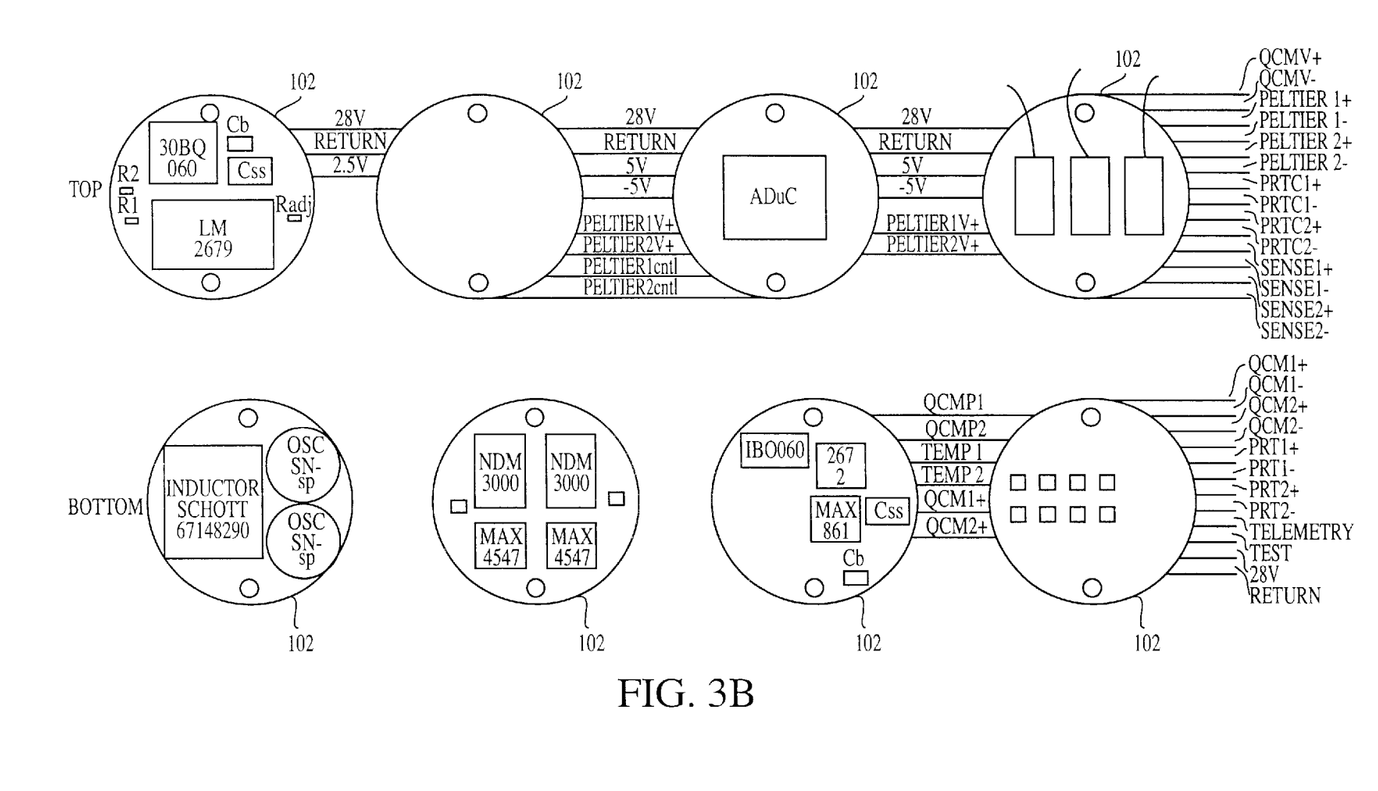
FIG. 3B is a detailed diagram of the various circuits in FIG. 3A.

FIG. 3B is a detailed diagram of the various circuit boards 102 shown in FIG. 3A and an example of their possible connections.

Figure 4:
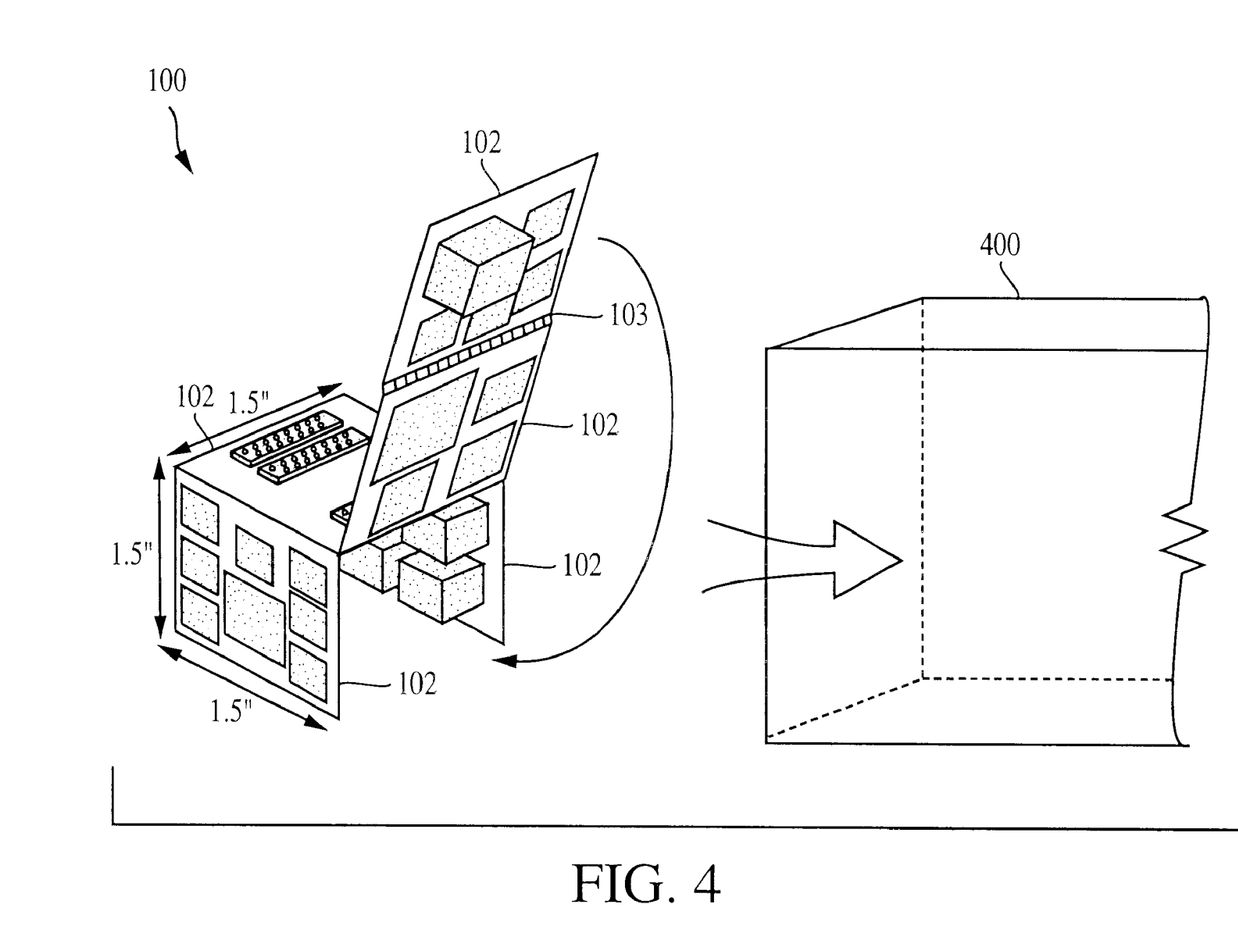
FIG. 4 is a three-dimensional diagram of the QCM controller apparatus according to the present invention.

FIG. 4 is a three-dimensional diagram of the QCM controller 100 apparatus according to the present invention. FIG. 4 shows the controller circuit boards 102 and connectors 103. Assembled as a cube, those circuits requiring a heat sink are located on the outside of the assembly. Further, the circuit boards 102 can be separated by function. This reduces cross talk and better isolates grounds compared to a single, flat circuit board. The QCM sensor 300 can be connected to the controller 100 by at least on cable 340 (FIG. 5).

Figure 5:
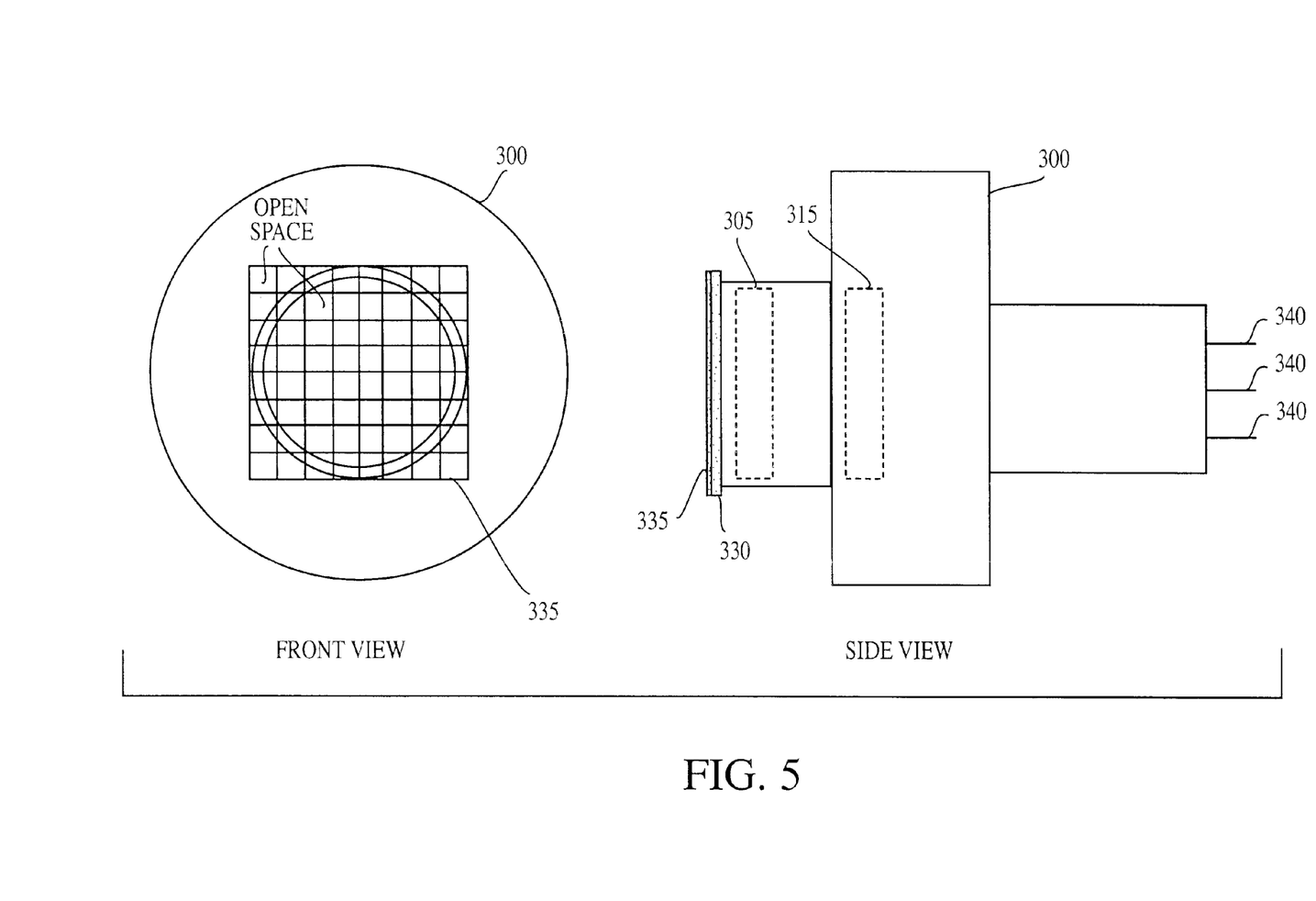
FIG. 5 is a diagram of the QCM sensor system high voltage grid according to the present invention.

FIG. 5 is a diagram of the QCM sensor system high voltage grid 335 according to the present invention. The grid 335 is placed over the face of the QCM sensor 300 between the outside environment and the first quartz crystal 305. Between the grid 335 and face of the QCM sensor 300 is an insulator 330. The grid 335 is charged (high voltage, low current) to a potential either above or below case ground. When the grid 335 is charged positive relative to the case ground, it attracts positive ions and repels negative ions. As the ions are attracted to the grid 335 they accelerate toward the QCM sensor 300. The interstitial space within the grid 335 is large enough to allow desired ions to pass through to the quartz crystal 305. In this example, QCM sensor 300 can be connected to microcontroller 100 using connectors 340, which can be nano-connectors, miniature wiring, or the equivalent.

Figure 6:
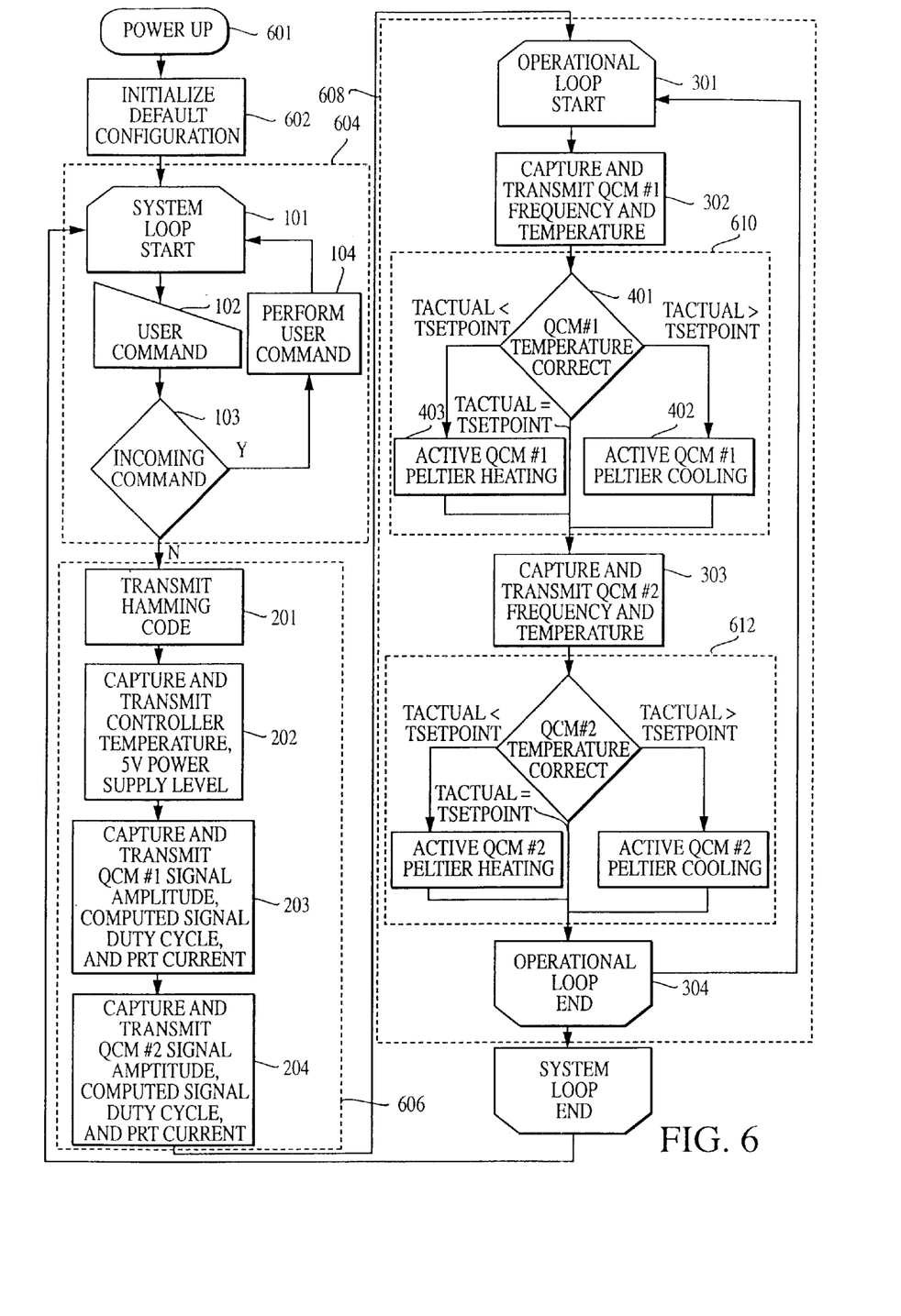
FIG. 6 is a flow chart explaining how the controller controls data acquisition and processing associated with the QCM sensor.

Once the system is initialized, a software subroutine 604 is executed. In the subroutine 604, step 101 starts the subroutine 604. Step 102 checks for incoming commands from a remote user 500 (FIG. 1), which is received from command interface uplink 115 (FIG. 2). Step 103 detects if the command is a new command. If so, step 104 performs the command and the subroutine starts again. If the command is not a new command, Step 103 then proceeds to subroutine 606 wherein, in step 201 the Hamming code is transmitted. Next, step 202 is executed. This step involves separate routines to capture signals associated with the microcontroller temperature monitor 150 and QCM power circuit 130. In this way, the temperature of the QCM controller 100 is detected and the voltage supply level to the QCM sensors 300 is checked. These signals are then transmitted to a remote user 500 (FIG. 1).

Steps 203 and 204 are then executed. These steps capture voltage and current signals associated with beat frequency signal conditioning circuits 120 and quartz crystal thermal monitor sources 145 of the respective QCM's. In this embodiment, the amplitude of the beat frequency voltage signal is detected, the duty cycle is detected, and the electrical current delivered to the QCM thermal monitor 310 is checked. Alternately, the period of the beat frequency signal can be detected. Further, sampling over a time period equal to several signal periods allows for an average period to be calculated. These signals are then transmitted to a remote user 500 (FIG. 1). Another subroutine 608 is then run. Step 301 initializes an operational loop. Step 302 then captures and transmits the frequency and temperature of one of the QCM sensors. This is done by capturing voltage signals associated with signal conditioning circuit 120 and QCM thermal monitor signal conditioning circuits 135. These signals are then transmitted to a remote user 500 (FIG. 1).

Subroutine 610 is then run to correct the temperature of the QCM sensor. The set-point temperature is set to the desired QCM sensor 300 operating temperature. The measured temperature is then compared in Step 401 to the set-point temperature. If the measured temperature is higher than the set-point temperature, step 402 adjusts the current to the thermal-electric heat pump circuit 140 by way of thermal electric heat pump controller 141 and switch 142, to slowly cool the QCM sensor system 300 at a set rate of change in temperature. If the measured temperature is lower than the set-point temperature, step 403 adjusts the current to the thermal-electric heat pump circuit 140 by way of the thermal electric heat pump controller 141 and switch 142, to slowly heat the QCM sensor system 300 at a set rate of change in temperature. If the measured temperature is equal to the set-point temperature, no adjustment is made. During thermal-gravitational analysis, the set-point temperature is set at a maximum value and the current to the thermal-electric heat pump circuit 140 is switched to heat the QCM sensor 300 at a slow rate.

Step 303 is then performed which is the same as step 302 but for the second QCM sensor 300. The subroutine 612 is then run. Subroutine 612 is the same as subroutine 610 except it is performed with respect to the second QCM sensor 300. When subroutine 612 is finished the operation loop is ended in step 304. In this example, the subroutine 608 is repeated 50 times, although this number can be adjusted by the remote user 500 in accordance with what is desired from the system. After step 304, the system loop is ended and the software-driven data acquisition and processing subroutines 604 and 606, are repeated starting with checking for incoming commands from a remote user 500 (FIG. 1).

Thus, the present invention provides a smaller, low power, flexible controller that is also less expensive. The controller of the present invention is modifiable by a user so that it can be reconfigurable during operation.

The foregoing is considered as illustrative only of the principles of the invention. Further, since numerous modifications and changes will readily occur to those skilled in the art, it is not desired to limit the invention to the exact construction and applications shown and described, and accordingly, all suitable modifications and equivalents may be resorted to, falling within the scope of the invention and the appended claims and their equivalents.

We claim:

1. A controller, for controlling an apparatus including a microelectronic microbalance sensor and for conditioning electronic signals having associated therewith electronic circuits and self-monitoring software, said controller comprising:

a controller thermal monitor, operatively connected to the apparatus, for detecting a temperature of the apparatus and outputting a controller temperature signal;

first temperature measuring means, operatively connected to said controller thermal monitor, for detecting said controller temperature signal from said controller thermal monitor;

second temperature measuring means, operatively connected to the apparatus, for detecting a temperature signal from the microelectronic microbalance sensor and outputting a current signal;

signal conditioning means, operatively connected to the microelectronic microbalance sensor, for receiving and conditioning a beat frequency signal from the microelectronic microbalance sensor;

a microcontroller, operatively connected to said controller thermal monitor, said first and second temperature measuring means, and said signal conditioning means, for converting the controller temperature signal, the microelectronic microbalance sensor temperature signal, said current signal, an amplitude of said beat frequency signal, a voltage from the microelectronic microbalance sensor, and said beat frequency signal into data records and for manipulating said data records for transmission.

2. The controller according to claim 1, said controller further comprising:

a thermal-electric hear pump circuit, operatively connected to said second temperature sensing means, for detecting said temperature signal from said second temperature sensing means and outputting an electric current and for heating and cooling the microelectronic microbalance sensor by switching the direction of said electric current in said thermal-electric heat pump circuit; and a power switch, operatively connected to the microelectronic microbalance sensor, for energizing and de-energizing and switching power to the microelectronic microbalance sensor.

* * * * *